United States Patent
Rosato et al.

[11] Patent Number: 5,951,522
[45] Date of Patent: Sep. 14, 1999

[54] HYPODERMIC NEEDLE SAFETY ENCLOSURE

[75] Inventors: Robert E. Rosato, West Chester, Pa.; Judy G. Stanek, Marlton, N.J.

[73] Assignee: Millennium Medical Distribution

[21] Appl. No.: 09/187,305

[22] Filed: Nov. 5, 1998

[51] Int. Cl.[6] .................................................. A61M 25/00
[52] U.S. Cl. .......................... 604/177; 604/192; 604/162
[58] Field of Search ................................... 604/174, 177, 604/187, 192, 162, 164, 167, 263

[56] References Cited

U.S. PATENT DOCUMENTS

| | | | |
|---|---|---|---|
| 4,611,382 | 9/1986 | Clark | 29/450 |
| 4,627,842 | 12/1986 | Katz | 604/177 |
| 4,631,058 | 12/1986 | Raines | 604/263 |
| 4,645,495 | 2/1987 | Vaillancourt | 604/180 |
| 4,676,783 | 6/1987 | Jagger et al. | 604/171 |
| 4,710,176 | 12/1987 | Quick | 604/177 |
| 4,813,939 | 3/1989 | Marcus | 604/177 |
| 4,820,282 | 4/1989 | Hogan | 604/263 |
| 4,935,011 | 6/1990 | Hogan | 604/177 |
| 4,941,881 | 7/1990 | Masters et al. | 604/162 |
| 4,969,876 | 11/1990 | Patterson | 604/171 |
| 5,085,639 | 2/1992 | Ryan | 604/110 |
| 5,120,320 | 6/1992 | Fayngold | 604/177 |
| 5,192,275 | 3/1993 | Burns | 604/263 |
| 5,330,438 | 7/1994 | Gollobin et al. | 604/177 |
| 5,350,368 | 9/1994 | Shields | 604/263 |
| 5,354,281 | 10/1994 | Chen | 604/177 |
| 5,505,711 | 4/1996 | Arakawa et al. | 604/171 |
| 5,531,704 | 7/1996 | Knotek | 604/192 |
| 5,584,813 | 12/1996 | Livingston et al. | 604/177 |
| 5,607,398 | 3/1997 | Parmigiani | 604/177 |
| 5,674,201 | 10/1997 | Steinman | 604/165 |
| 5,706,520 | 1/1998 | Thornton et al. | 2/21 |

*Primary Examiner*—John D. Yasko
*Attorney, Agent, or Firm*—Jack C. Munro

[57] ABSTRACT

A hypodermic needle safety enclosure which is designed principally for a hypodermic needle that is located in the shape of a right angle. The hypodermic needle has mounted thereon a wing assembly which can take the form of a single integral member having a plurality of spaced apart fold lines which permits the integral member to be folded between a mounting position and a protective position or a pair of wing members which are mounted in a scissors arrangement which is movable between a mounting position and a protective position. Within both embodiments of safety enclosure, upon withdrawing of the needle from the installed position within the body of a human, the wing assembly is automatically positioned to encase the sharpened point of the needle thereby preventing undesired injury by the needle to the medical practitioner that is installing and removing of the enclosure.

11 Claims, 5 Drawing Sheets

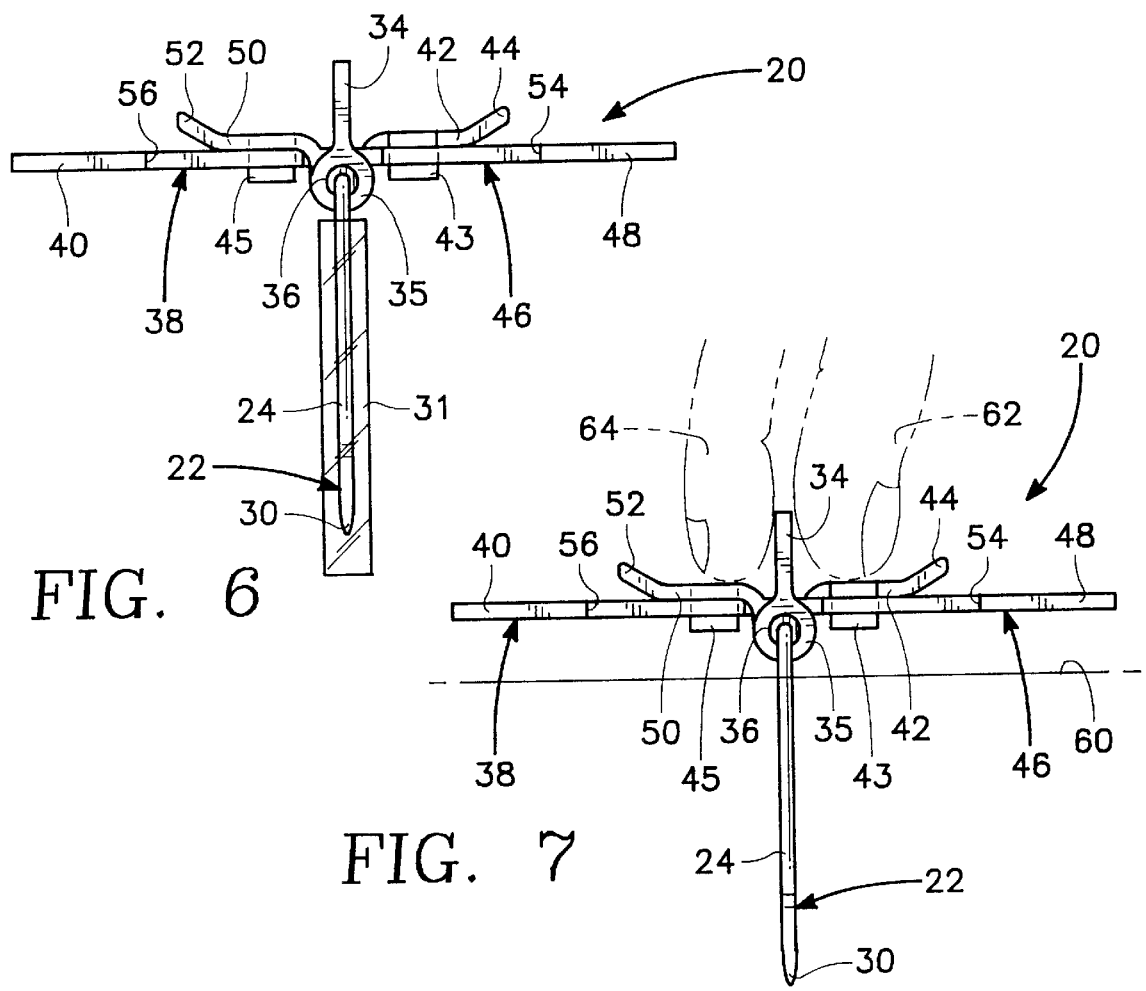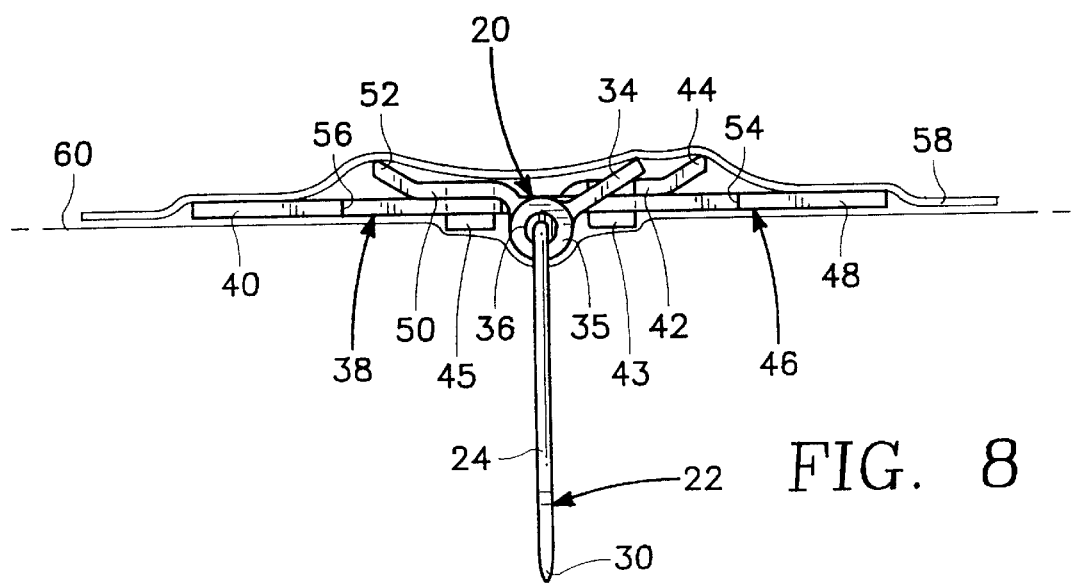

HYPODERMIC NEEDLE SAFETY ENCLOSURE

BACKGROUND OF THE INVENTION

1) Field of the Invention

The field of this invention is directed to a safety enclosure for a hypodermic needle that has a fore end that assumes an angular position relative to the aft end of the needle.

2) Description of the Prior Art

Within the medical field, more and more patients require the use of vascular access devices as part of their care. Vascular access devices are used on the patients to supply pain drugs, chemotherapy, antibiotics, antiviral or antifungal drugs as well as for hydration and nutrition. In recent years, there has been a substantial increase in the number of patients with implanted ports. An implanted port requires a special needle to be inserted through the skin of the patient and into the port. The most common type of such needle includes a ninety-degree bend. Because of the configuration of the needle, removing the needle at the end of the infusion therapy is particularly dangerous exposing the medical practitioner to a high degree of risk of needlestick injury.

Implanted ports were first introduced in the early 1980's. These vascular access devices are surgically placed under the surface of the skin. The implanted port consists of a catheter and a reservoir. The placement requires a minor surgical procedure with the catheter being threaded into a vein with the reservoir then being placed in a subcutaneous pocket of the body. A common location of such a subcutaneous pocket would be in the anterior upper chest wall below the clavicle. The top of the port, called the septum, is made of a rubber or self-sealing silicon. It is through this part of the port that an infusion needle is inserted for filling the reservoir of the port or aspirating blood or fluid. The septum allows the needle to enter, holds the needle in place, stabilizes the needle during infusion therapy and reseals once the needle is removed.

In order to extend the life of the usage of the septum, damage to the septum is to be minimized even after repeated punctures by a needle. To minimize the damage to the septum, a non-coring needle is preferred. A traditional needle will poke a hole and result in leaks from the septum only after a few punctures prematurely ending the life of the port. A non-coring needle pierces the septum like a knife so that upon removal, the septum can seal itself cleanly. These special non-coring needles are commonly called a Huber needle. Non-coring needles also prevent fragmentation of the septum material (rubber or silicone) that could lead to occlusion of the infusion catheter attached to the port or infusion of fragment(s) into the vein of the patient.

Huber needles are designed in different lengths and different configurations. Straight needles are used for flushing the port, drawing blood or administering bolus injections. Needles bent at a ninety degree right angle are used for longer term infusion therapy. This angle relationship of the needle allows the Huber needle to be more safely anchored to the skin around the port. These needles are commonly left in place for a period of several days. Both straight and right angle Huber needles commonly have "wings" alongside the needle with these wings being used for securing the Huber needle to the patient by taping the wings to the skin of the patient plus facilitating insertion and removal.

Implanted ports have advantages such as reduced risk of infection, no need for a dressing, no need to restrict activities of the patient permitting the patient to normalize their lives. However, the implanted port has one significant disadvantage, and that is there is a high degree of needlestick injury during removal of the Huber needle by the medical practitioner. It is estimated that there are probably in excess of 850,000 needlestick injuries in the medical field each and every year. In conjunction with needlestick injuries, there is a risk of the medical practitioner acquiring a disease such as aids or hepatitis. Although it may be said that it is the carelessness of the medical practitioner that results in a needlestick injury, it has been shown in the past that constructing needles to be safer substantially reduces the number of needlestick injuries eliminating the asking of the medical practitioners to make behavioral changes in the way of handling hypodermic needles. The difficulty of the removal of the needle, rather than carelessness, is what commonly causes needlestick.

The procedure of removing a Huber needle commonly produces what is known as bounce-back which comprises a rebounding effect. Bounce-back is an action which by pulling on the needle or needle attachment, the sharpened end of the needle hooks into the port. This hooking of the needle is due to a snag occurring impeding the removal of the needle from the septum. The medical practitioner thus pulls harder contracting the muscles of his or her arm. When the needle is finally released, the muscles relax and an opposite movement takes place and drives the Huber needle point down into the non-dominant hand of the medical practitioner thus causing the common form of needlestick injury.

Two devices have been on the market to help reduce the risk of needlestick injury. One device consists of a protective device that fits over the port. The nurse then uses a hemostat to pull the needle up into the device for containment during removal of the needle from the patient. The device and the needle is then disposed of. One disadvantage of this device is that it requires a significant change in technique having to do with the removal of a Huber hypodermic needle, and it also requires the use of additional equipment, the hemostat, and its use requires a significant amount of dexterity.

A second device is a scissors-type device formed of two blades which are slid under wings of the needle and against the patient's skin. When the needle is being removed, the bottom blade of the device stabilizes the device while the upper blade pulls out the needle. The needle is held in the blade but the sharp end remains exposed. This device also requires a significant change in technique and has a further disadvantage in that it does not fully contain the sharp end of the needle.

There is also a device called a Huberloc™. Also the Huberloc™ device requires a change in technique but it does eliminate pulling a bare needle out of a port. Also, the Huberloc™ has the advantage that it does fully contain the sharp end of the needle. Also, the Huberloc™ requires the usage of additional equipment which comprises a plastic holder to be used in conjunction with the needle.

SUMMARY OF THE INVENTION

A desirable feature of the present invention is to construct a hypodermic needle safety enclosure which permits hypodermic needles to be installed and removed in the normal conventional manner while at the same time eliminating the possibility of needlestick injury.

Another advantage of the present invention is to construct a hypodermic needle safety enclosure which can be manufactured at a relatively inexpensive cost and therefore sold to the medical industry at a reasonable price with costs now being in the medical industry a significant factor as to whether or not a product will be used.

The hypodermic needle safety enclosure of the present invention takes the form of a wing assembly which is mounted onto the aft end of an angularly shaped hypodermic needle. A typical angular configuration would be where the fore end of the needle assumes a ninety degree position relative to the aft end of the needle. The wing assembly is mounted on the aft end of the needle. The wing assembly is movable between a mounting position and a protective position. The mounting position locates the wing assembly substantially transverse to the fore end and spaced from the sharpened point of the needle. The protective position locates the wing assembly to encase the sharpened point of the needle preventing penetration of the sharpened point into the hand of the medical practitioner. The wing assembly can comprise a single integral member having a plurality of spaced apart fold lines which divides the single integral member into a plurality of interconnected panels, or the wing assembly can comprise a pair of wing members mounted in a scissor arrangement which forms a pair of opposed handle tabs when the wing assembly is in the mounting position. Each handle tab has a flared end which facilitates manual contact and pivoting movement of the wing members from a mounting position to the protective position. The single integral member may have a locking arrangement which locks the wing assembly in the protective position preventing movement from the protective position back toward the mounting position during disposal of a hypodermic and the safety enclosure.

BRIEF DESCRIPTION OF THE DRAWINGS

FIG. 6 is a front view of a second embodiment of hypodermic needle safety enclosure of the present invention showing the second embodiment in the position prior to initiating installation;

FIG. 7 is a view similar to FIG. 6 depicting the installation of the hypodermic needle;

FIG. 8 is a view similar to FIG. 7 but showing the second embodiment of hypodermic needle safety enclosure of the present invention being fixedly secured onto the body of the patient by means of adhesive tape;

DETAILED DESCRIPTION OF THE PREFERRED EMBODIMENT

Figure 1:
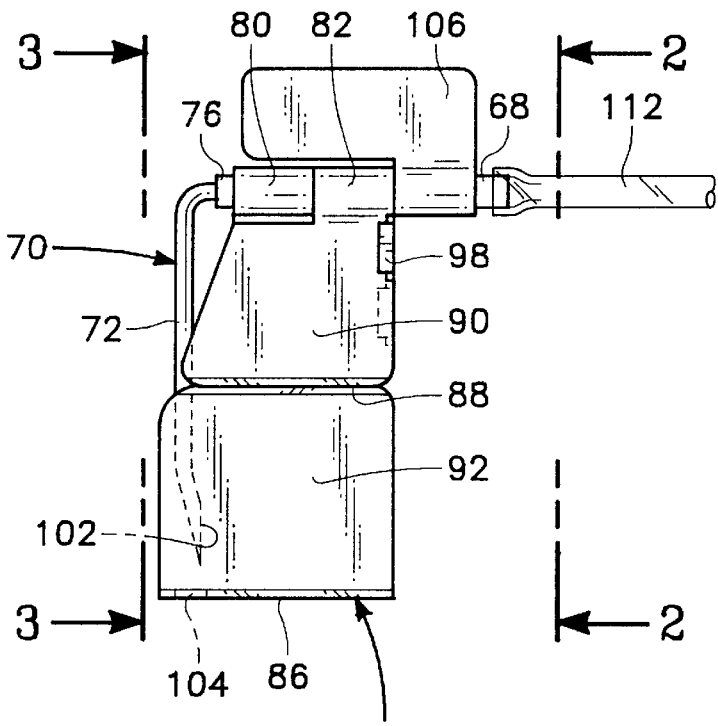
FIG. 1 is a side elevational of the first embodiment of hypodermic needle safety enclosure of the present invention showing the safety enclosure in the protective position.

Referring particularly to the drawings, there is shown in FIGS. 1 to 5 the first embodiment 66 of hypodermic needle safety enclosure of the present invention. The first embodiment 66 is to be mounted on the aft end 68 of a hypodermic needle 70 such as a Huber needle. The hypodermic needle 70 includes a fore end 72 which is angularly disposed at approximately ninety degrees relative to the aft end 68. The hypodermic needle 70 has a through fluid conducting passage 74. A stop sleeve 76 is fixedly mounted onto the aft end 68 defining the forward limit of movement of the wing assembly 78. The wing assembly 78 is composed of a single integral member the ends of which are formed into short tubes 80 and 82. The short tubes 80 and 82 are to be in alignment with each other and the aft end 38 is conducted through the short tubes 80 and 82. The wing assembly 78 includes three in number of spaced-apart cutout fold lines 84, 86 and 88. Between the short tube 82 and the fold line 88 is formed a panel 90. Between the fold line 88 and the fold line 86 is located a panel 92. A panel 94 is located between the fold line 86 and the fold line 84. A similar panel 96 is located between the short tube 80 and the fold line 84. It is to be understood that the fold lines 84, 86 and 88 are all parallel. The fold lines 84, 86 and 88 could comprise "living hinges" if the second embodiment 66 is constructed of plastic.

Figure 2:
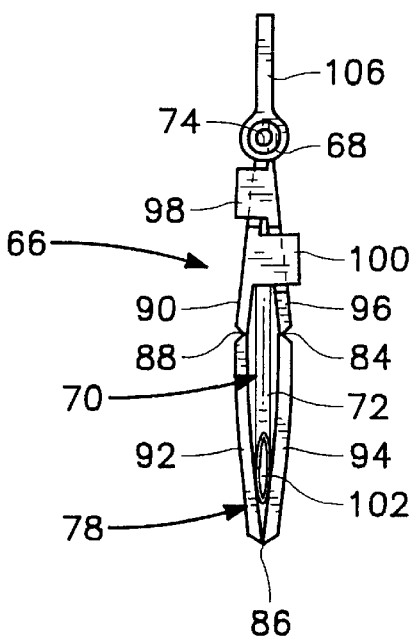
FIG. 2 is a rear view of the first embodiment of hypodermic needle safety enclosure of the present invention taken along line 2—2 of FIG. 1.
Figure 3:
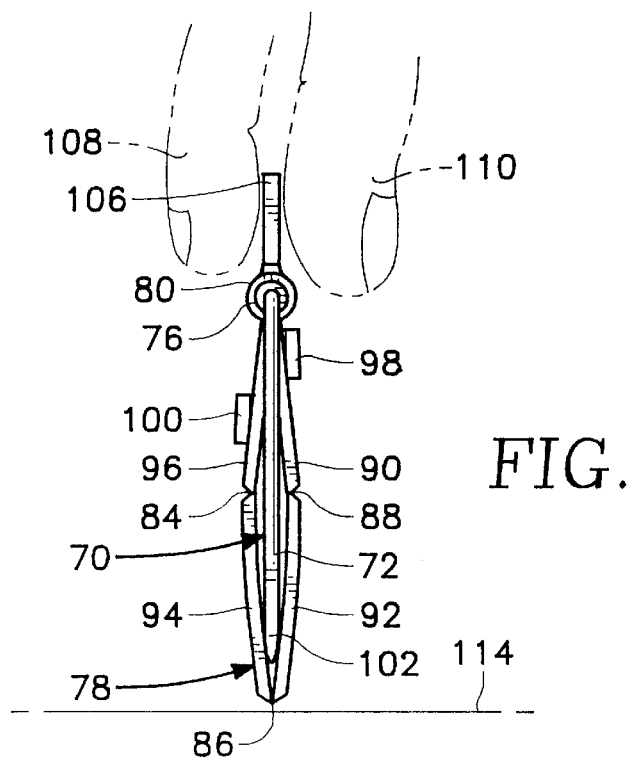
FIG. 3 is a front view of the first embodiment of hypodermic needle safety enclosure of the present invention taken along line 3—3 of FIG. 1.
Figure 4:
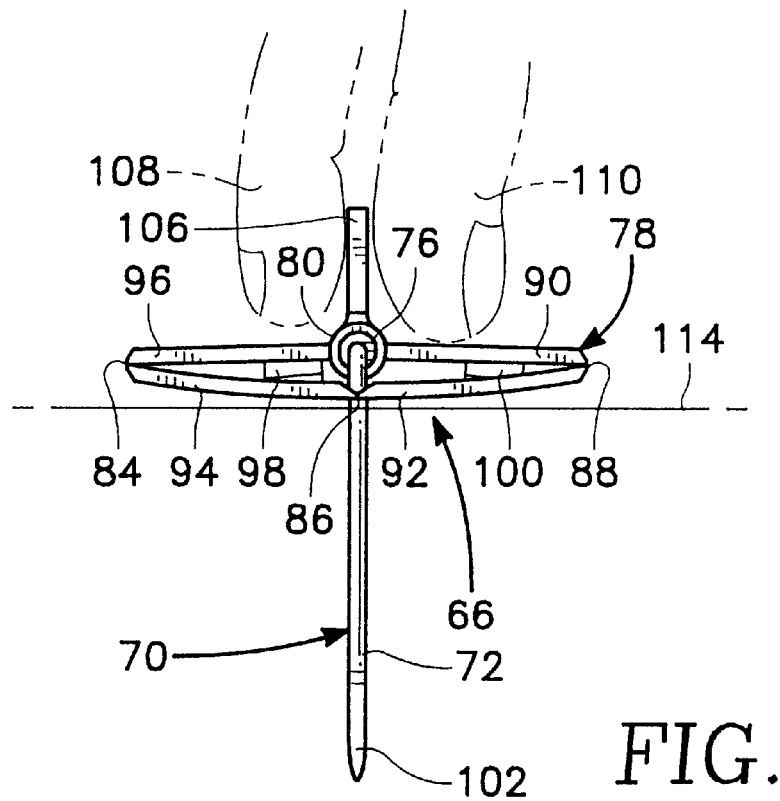
FIG. 4 is a front view similar to FIG. 3 but showing the first embodiment of hypodermic needle safety enclosure of the present invention in the mounting position rather than the protective position of FIG. 3.
Figure 5:
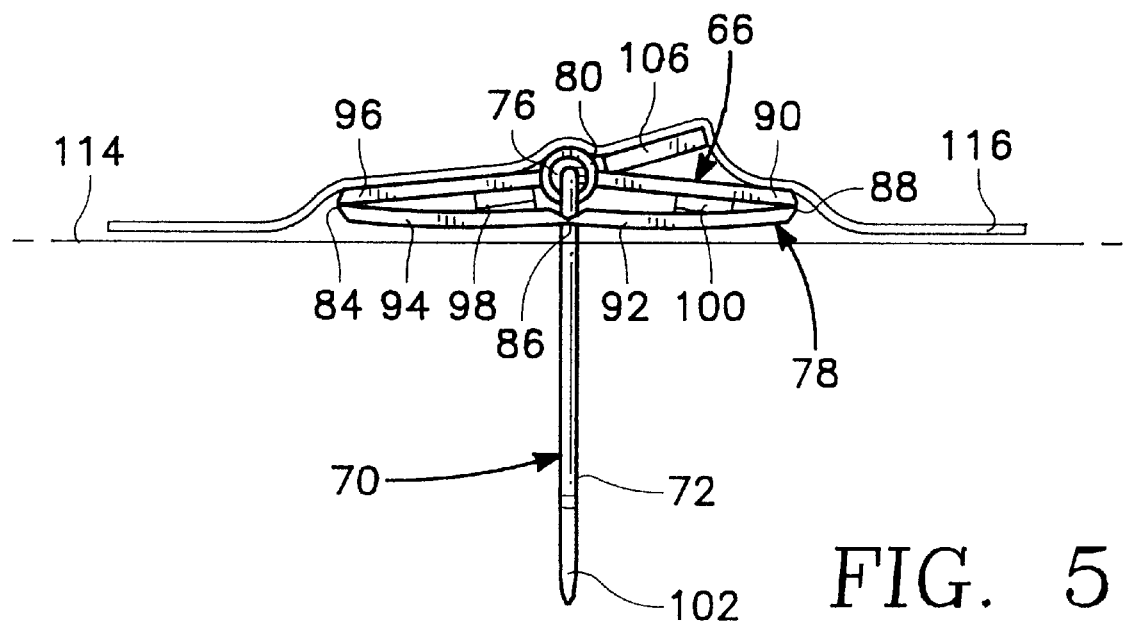
FIG. 5 is a view similar to FIG. 4 of the first embodiment of hypodermic needle safety enclosure of the present invention showing the first embodiment being adhesively secured onto the body of the patient.
Figure 9:
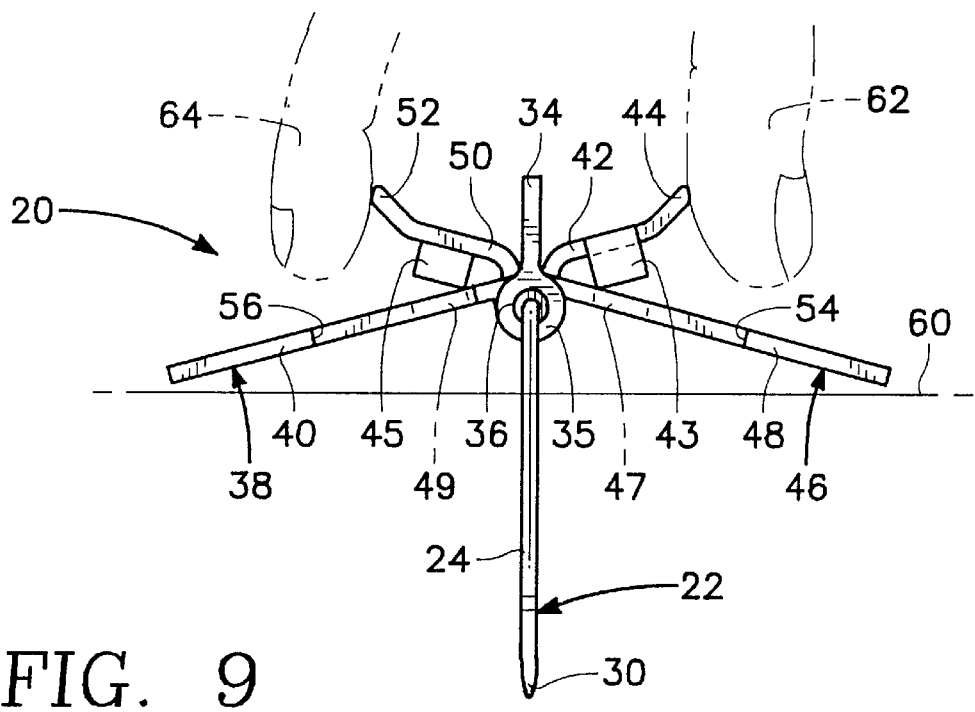
FIG. 9 is a front view of the second embodiment of hypodermic needle safety enclosure of the present invention depicting movement of the safety enclosure from the installed position toward the protective position.

Fixedly mounted onto the panel 96 is a locking tab 98. A similar such locking tab 100 is fixedly mounted onto the panel 90. The locking tab 98 includes an inward protrusion (not shown) which is to override the edge of the panel 90 when the first embodiment 66 is in the protective position as shown in FIGS. 1–3 of the drawings. At the same time, the locking panel 100 overrides the edge of the panel 96. Therefore, the locking tabs 98 and 100 function to lock and hold the wing assembly 78 in the protective position so as to keep the sharpened point 102 of the fore end 72 of the hypodermic needle 70 encased between the panels 92 and 94 when in the protective position. It is to be noted that the cutout fold line 86 includes a hole 104 through which the sharpened point 102 and the fore end 72 of the hypodermic needle 70 is to be conducted when moving from the protective position to the mounting position as shown in FIGS. 4 and 5. Also pivotally mounted on the aft end 68 of the hypodermic needle 70 is a handle fin 106. It is to be noted that the shape of the handle fin 106 is that of an L shape with a portion of the handle fin 106 overlying the short tubes 80 and 82. When grabbing of the handle fin 106, it is desirable to have ones finger 108 and thumb 110 located close to being in alignment with the fore end 72 of the hypodermic needle 70. The aft end 68 is connected to a flexible tube 112 through which liquid is to be conducted in a similar manner as was previously discussed in relation to flexible tube 32.

When the medical practitioner removes the first embodiment 66 of this invention from its package (not shown), the first embodiment 66 will probably be in the position shown in FIG. 4 with the sharpened point 102 covered by a plastic tube (not shown), with the wing assembly 78 folded about fold lines 84 and 88 and not folded about fold line 86. The not shown plastic tube is then removed from the sharpened point 102 and discarded. The medical practitioner first grasps with one hand the handle fin 106 by fore finger 108 and thumb 110. The medical practitioner begins to insert the sharpened end 102 into the body 114 of the patient and, upon achieving complete insertion, panels 92 and 94 will be located against the body 114. The position of the first embodiment 66 will be as shown in FIGS. 4 and 5 of the drawings. Once properly installed, a section of adhesive tape 116 is then placed over the first embodiment 66 as shown in FIG. 5 with complete securement now being obtained of the second embodiment 66 onto the body 114. When securing of the adhesive tape 116, the handle fin 106 is pivoted to either directly adjacent the panel 90 or the panel 96 so that it does not protrude.

In order to effect removal of the hypodermic needle 70 from the body 114, the medical practitioner first removes and discards adhesive tape 116. The medical practitioner then squeezes the fold lines 84 and 88 together which will cause the fold line 86 to move away from tube 80 and thereby pull the sharpened end 102 out of the port and out of the patient's skin 114 in a slow and controlled manner. Upon complete removal of the needle 70, the medical practitioner will then apply a squeezing together action between panels 90 and 96 which will cause the locking tabs 98 and 100 to engage and lock in position thereby lockingly restraining the wing assembly 78 in the protective position as shown in FIGS. 1–3 of the drawings. Normally, the first embodiment 66 of this invention, as well as the hypodermic needle 70, is then discarded.

Referring particularly to FIGS. 6–14 of the drawings, there is shown the second embodiment 20 of hypodermic needle safety enclosure of this invention. The second embodiment 20 has a hypodermic needle 22 such as a Huber needle. The hypodermic needle 22 has a fore end 24 and an aft end 26. Both the fore end 24 and the aft end 26 are integral and each comprise a thin, tubular member which has a through passage 28. The liquid is able to be conducted through the passage 28. The fore end 24 terminates in a sharpened point 30. The aft end 26 is to be attached to a flexible tube 32.

Pivotally mounted on the aft end 26 is tubular member 35 of a handle fin 34. A stop sleeve 36 is fixed on the aft end 26 and abuts against the front end of the tubular member 35 to prevent any sliding movement of the handle fin 34 in the direction of the fore end 24. The function of the handle fin 34 will be explained further on in the specification. Also pivotally mounted on the aft end 26 by a tubular member 41 and abutting against the handle fin 34 is a wing member 38. Wing member 38 includes a main section 40 and a handle tab 42. The handle tab 42 has a flared outer end 44.

Also pivotally mounted by a tubular member 51 on the aft end 26 is a wing member 46 which is basically of a similar configuration to wing member 38 but being reversed. The wing member 46 includes a main section 48 and a handle tab 50. The outer end of the handle tab 50 is defined as a flared end 52.

It is to be noted that the main section 48 defines a large cutout 54. A similar large cutout 56 is formed in the main section 40. The cutouts 54 and 56 are to be in alignment when the first embodiment 20 is in the protective position shown in FIGS. 1–3 of the drawings. This will permit the handle fin 34 to be pivoted within the confines of the cutouts 54 and 56 if such is deemed to be desired by the medical practitioner. However, in normal operation, once the second embodiment 20 is in the mounting position, as shown in FIGS. 7 and 8 of the drawings, the handle fin 34 is pivoted to within the confines of either the cutout 54 or 56 in order to place the handle fin 34 in a nonprotruding position facilitating the installation of adhesive tape 58 over the entire first embodiment 20 installing such on the body 60 of the patient. The tubular member 35 presses into the body 60. Wing members 38 and 46 may be made from a molded semi-rigid plastic such as polypropylene, polyethylene or polyurethane that is flexible enough to bend/flex when taped to the patient's skin but is rigid enough to allow removal of the needle from the implanted vascular port and the patient's skin by squeezing flared outer ends 44 and 52 together.

The operation of the second embodiment 20 of this invention is as follows: The second embodiment 20 when removed from the package (not shown) within which it has been supplied, will be in the position shown in FIG. 6 of the drawings. The medical practitioner, to install the second embodiment 20, grabs with one hand, indicated by thumb 62 and forefinger 64, the handle pin 34 and removes protective tube 31 from the needle 24 and discard such. The medical practitioner then proceeds to insert the sharpened end 30 into the body 60 of the patient to the desired depth as is depicted in FIG. 7. The desired depth will be with the main sections 40 and 48 being flush against the body 60. The adhesive tape 58 is then applied then fixing in position preventing accidental dislodgment of the second embodiment 20 from its installed position.

The second embodiment 20 is then left for a period of time, which is generally several days, in this installed position and the needle 22 is then used to either supply fluids into the septum of the port within which it is installed (which is not shown) or is used to extract fluids from the septum.

Figure 10:
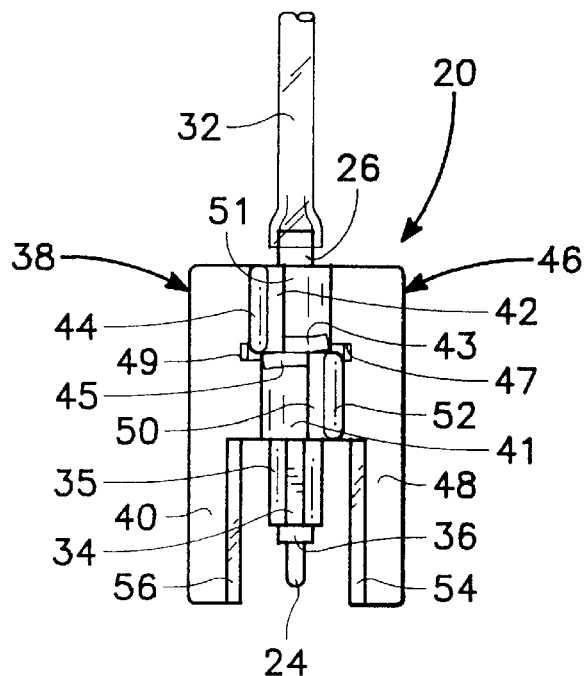
FIG. 10 is a top view of the second embodiment almost in the protective position showing deflection of the locking tabs.
Figure 11:
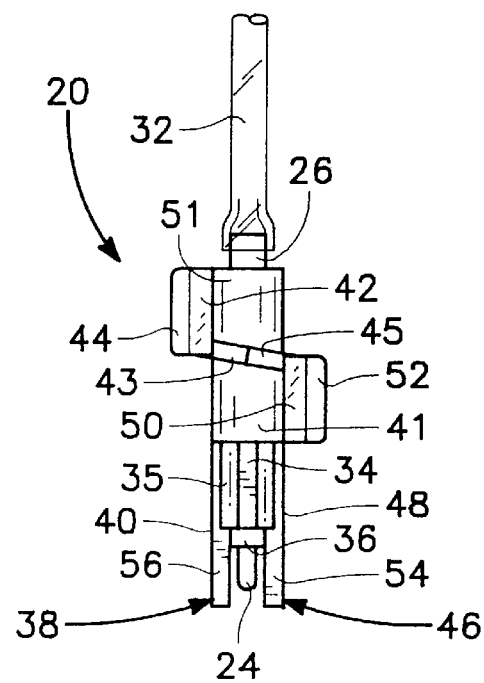
FIG. 11 is a view similar to FIG. 10 showing the second embodiment in the protective position.
Figure 12:
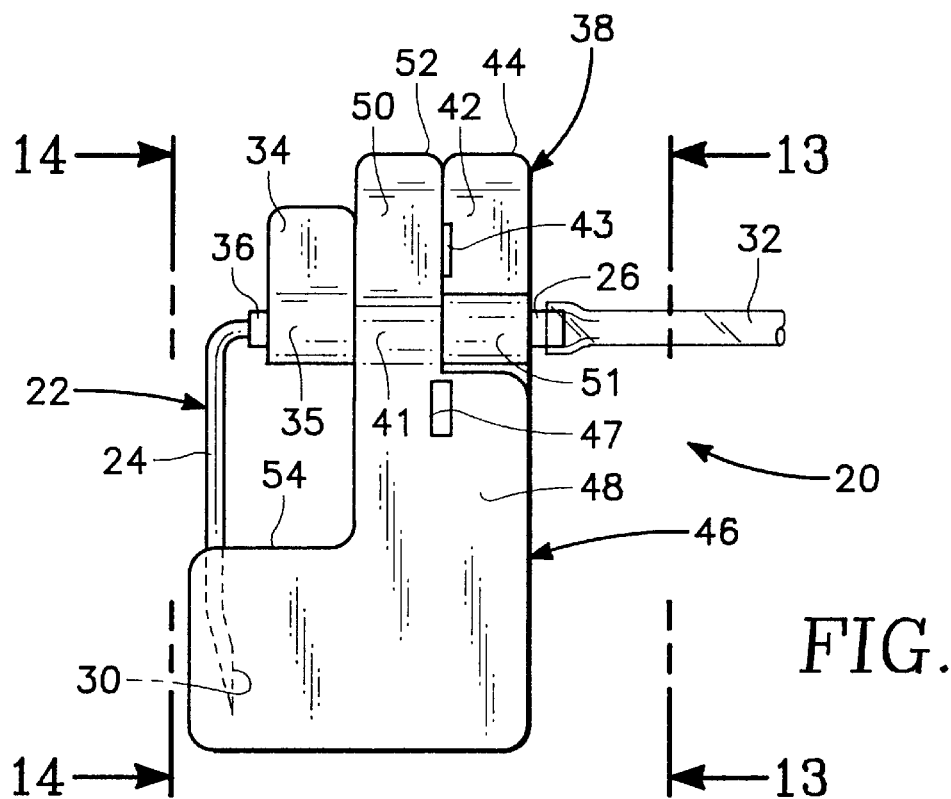
FIG. 12 is a side elevational view of the second embodiment in the protective position.
Figure 13:
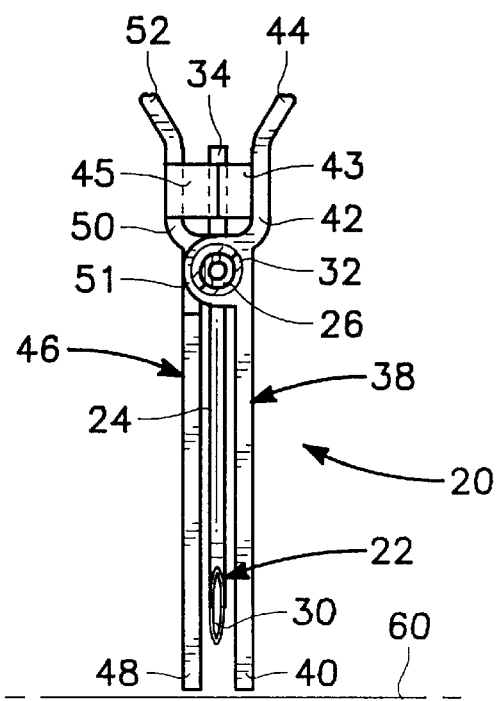
FIG. 13 is a rear view taken along line 13—13 of FIG. 12.
Figure 14:
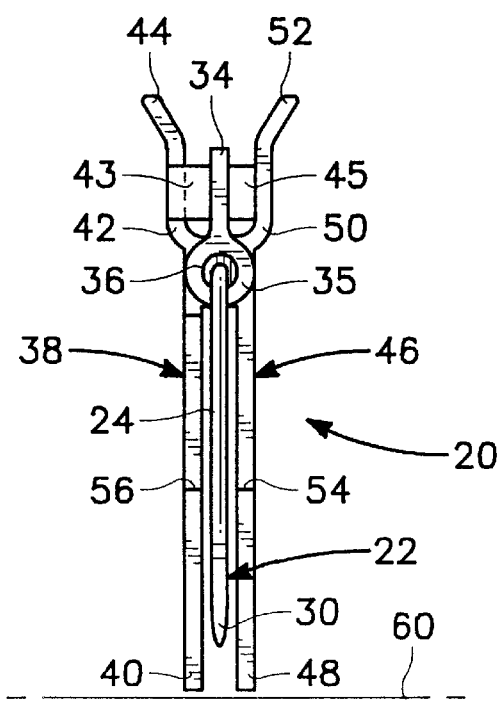
FIG. 14 is a front view taken along line 14—14 of FIG. 12.

Now let it be assumed that it is desirable to remove the first embodiment 20 from the installed position. The medical practitioner first removes the adhesive tape 58 and discards such. The medical practitioner then grabs an applies a squeezing action against the flared ends 44 and 52 which will cause the main sections 40 and 48 to pivot on the aft end 26. The main sections 40 and 48 will apply pressure against the body 60 and this pressure will result in a withdrawing action of the fore end 24 of the needle from the body 60. About the time the sharpened end 30 begins to withdraw completely from the body 60, the main sections 40 and 48 will be located at a rather acute angle relative (as shown in FIG. 10) to each other so that upon immediate withdrawal of the sharpened end 30 from the body 60, the main sections 40 and 48 will, in essence, slam shut clamping against opposite sides of the sharpened end 30 of the hypodermic needle 22. This will locate the main section 40 on one side of the fore end 24 of the hypodermic needle 22 and the main section 48 on the opposite side of the fore end 24 of the hypodermic needle 22. In essence, the sharpened point 30 is encased by the main sections 40 and 48. This encasement prevents the sharpened point 30 from accidentally puncturing the body of the medical practitioner prior to its disposal.

It is desirable to lock the encasement of the needle 22 and prevent the encasement from accidentally opening prior to the second embodiment 20 and the needle 22 being discarded. In order to accomplish this, there is mounted on the sidewall of the handle tab 42 and locking tab 43. A similar locking tab 45 is mounted on the sidewall of the handle tab 50. When the second embodiment 20 approaches the protective position as shown in FIG. 10, the locking tabs 43 and 45 abut each other and each deflect a short distance permitting each of the locking tabs 43 and 45 to pass during movement of the handles tabs 42 and 50 to their position when the second embodiment 20 is in the protective position. When the second embodiment 20 is in the protective position, the locking tabs 43 and 45 are no longer abutting which results in the locking tabs 43 and 45 springing back to their normal inclined position which results in the locking tabs 43 and 45 abutting against each other preventing any movement from the protective position toward the installing position shown in FIGS. 7 and 8. This locking position of the locking tabs 43 and 45 is clearly shown in FIG. 11.

When the second embodiment 20 is in the installing position shown in FIGS. 6–8, the locking tab 43 will extend through a hole 47 formed within main section 48. In a similar manner, the locking tab 45 will extend within a hole 49 formed within the main section 40.

It is to be noted that the amount of pivoting of the handle tabs 42 and 50 is each about ninety degrees. From the protective position encasing the sharpened end 30 of the hypodermic needle 22, the main sections 40 and 46 can be moved to be in substantial alignment as is clearly shown in FIGS. 4 and 10.

What is claimed is:

1. In combination with a hypodermic needle having a fore end and an aft end, said fore end terminating in a sharpened point, said aft end adapted to connect with a tube, said fore end comprises a thin, lineal, rigid, hollow, tubular member which is connected to said aft end which also comprises a thin, lineal, rigid, hollow, tubular member, said fore end being angularly disposed relative to said aft end, the improvement comprising:

a wing assembly mounted on said aft end, said wing assembly being movable between a mounting position and a protective position, said mounting position locates said wing assembly substantially transverse to said fore end and spaced from said sharpened point, said protective position encasing said sharpened point preventing penetration of said sharpened point into a body of a human, whereby with said wing assembly in said mounting position, said wing assembly is to be placed against the body of a human and fixed in place by a separate securing means with said needle installed in the body, whereby said wing assembly is to be manually moved from said mounting position to said protective position which will automatically withdraw said needle from the body and encase the sharpened point within said wing assembly.

2. The combination as defined in claim 1 wherein:

said fore end being angularly disposed substantially at a right angle relative to said aft end.

3. The combination as defined in claim 1 wherein:

said wing assembly including a locking means to lock said position of said wing assembly when in said protective position.

4. The combination as defined in claim 1 wherein:

said wing assembly including a handle fin pivotally mounted on said aft end, sand handle fin being graspable by a human user facilitating installation of said needle within a body of a human.

5. The combination as defined in claim 1 wherein:

said wing assembly comprising a pair of wing members mounted in a scissors arrangement forming a pair of opposed handle tabs when said wing assembly is in said mounting position, each said handle tab having a flared end in order to facilitate manual connection and pivoting movement of said wing members from said mounting position to said protective position resulting in said opposed handle tabs now being located in juxtaposition.

6. The combination as defined in claim 1 wherein:

said wing assembly comprising a single integral member having a plurality of spaced apart fold lines which divide said integral member into a plurality of interconnected panels.

7. The combination as defined in claim 6 wherein:

said wing assembly including a locking means to lock said position of said wing assembly when in said protective position.

8. The combination as defined in claim 7 wherein:

said wing assembly including a handle fin pivotally mounted to said aft end, said handle fin being graspable by a human user facilitating installation of said needle within a body of a human.

9. The combination as defined in claim 8 wherein:

said fore end being angularly disposed substantially at a right angle relative to said aft end.

10. The combination as defined in claim 5 wherein:

said wing assembly including a handle fin pivotally mounted to said aft end, said handle fin being graspable by a human user facilitating installation of said needle within a body of a human.

11. The combination as defined in claim 10 wherein:

said fore end being angularly disposed substantially at a right angle relative to said aft end.

* * * * *